United States Patent [19]

Crittenden et al.

[11] Patent Number: 5,201,754
[45] Date of Patent: * Apr. 13, 1993

[54] BALLOON DILATATION CATHETER WITH VARYING RADIOPACITY

[75] Inventors: James F. Crittenden, Hollis, N.H.; Bryan J. White, Lowell, Mass.

[73] Assignee: C. R. Bard, Inc., Murray Hill, N.J.

[*] Notice: The portion of the term of this patent subsequent to Apr. 17, 2007 has been disclaimed.

[21] Appl. No.: 475,417

[22] Filed: Feb. 2, 1990

Related U.S. Application Data

[60] Continuation-in-part of Ser. No. 303,908, Jan. 30, 1989, Pat. No. 4,917,088, which is a division of Ser. No. 729,541, May 2, 1985, Pat. No. 5,102,390.

[51] Int. Cl.[5] ............................................. A61M 29/02
[52] U.S. Cl. ..................................... 606/194; 604/96; 604/100
[58] Field of Search ............................... 606/194, 198; 604/96-103, 280, 95

[56] References Cited

U.S. PATENT DOCUMENTS

| | | | |
|---|---|---|---|
| 4,346,698 | 8/1982 | Hawson et al. | 604/194 |
| 4,538,622 | 9/1985 | Samson et al. | 128/772 |
| 4,545,390 | 10/1985 | Leary | 128/772 |
| 4,554,929 | 11/1985 | Samson et al. | 128/772 |
| 4,619,274 | 10/1986 | Morrison | 128/772 |
| 4,723,936 | 2/1988 | Buchbinder et al. | 604/194 |
| 4,748,986 | 6/1988 | Morrison et al. | 128/772 |
| 4,763,647 | 8/1988 | Gambale | 128/657 |
| 4,773,432 | 9/1988 | Rydell | 128/772 |
| 4,838,268 | 6/1989 | Keith et al. | 604/96 |
| 4,867,173 | 9/1989 | Leoni | 128/772 |
| 4,917,088 | 4/1990 | Crittenden | 604/96 |
| 4,922,924 | 5/1990 | Gambale et al. | 128/772 |
| 5,102,390 | 4/1992 | Crittenden et al. | 604/96 |

*Primary Examiner*—Stephen C. Pellegrino
*Assistant Examiner*—Michael Rafa
*Attorney, Agent, or Firm*—Wolf, Greenfield & Sacks

[57] ABSTRACT

A balloon dilatation catheter, usable in percutaneous transluminal angioplasty, is formed so that portions of the catheter both distally and proximally of the balloon have varyinq degrees of radiopacity. A portion of the catheter distally of the balloon presents a dark image under fluoroscopy while a portion located proximally of the balloon displays a moderately radiopaque image under fluoroscopy. The portion of the catheter in the region of the balloon may have a moderate, light or no radiopaque means.

11 Claims, 3 Drawing Sheets

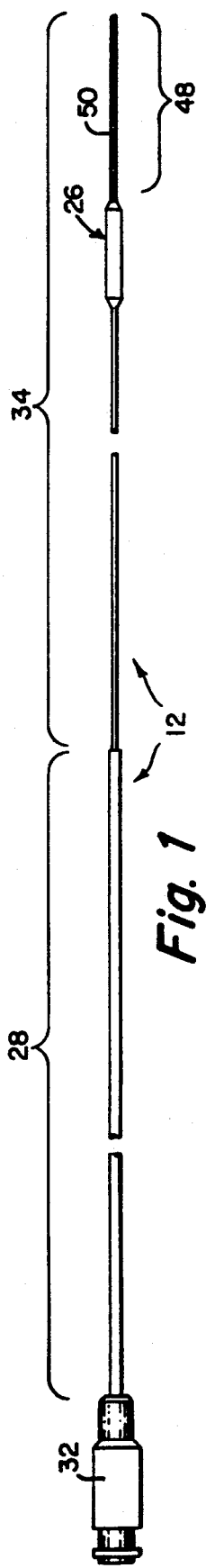
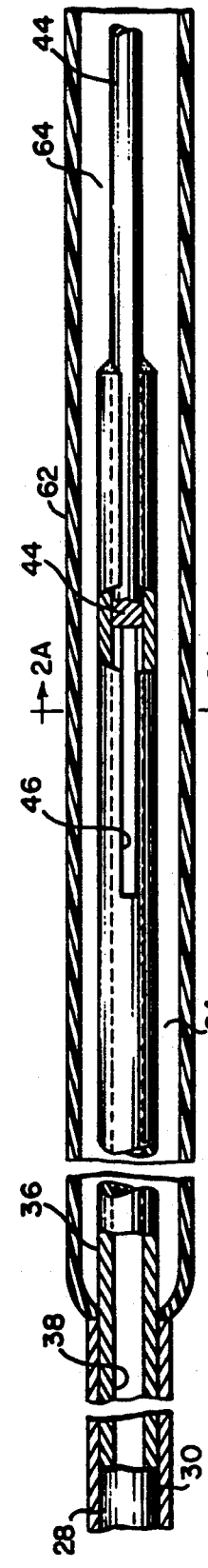
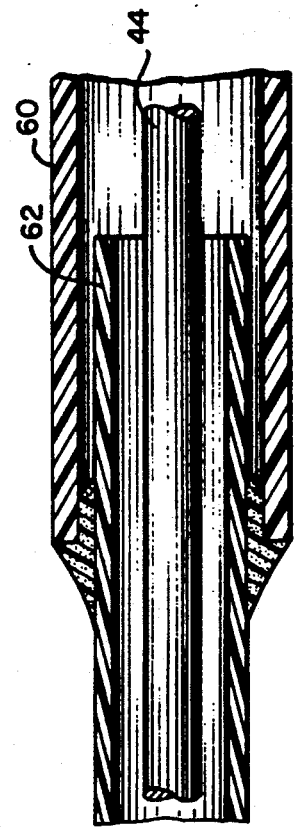

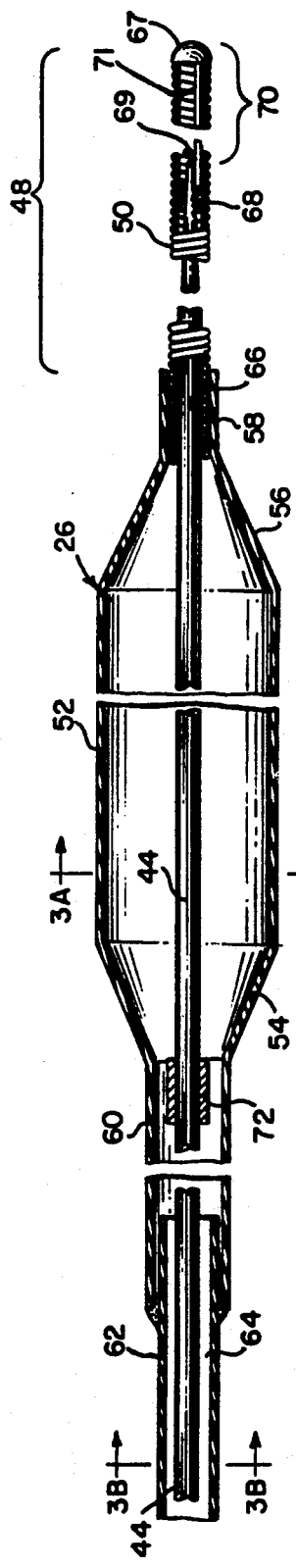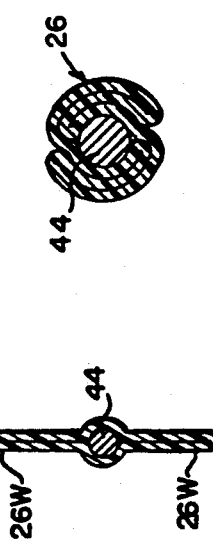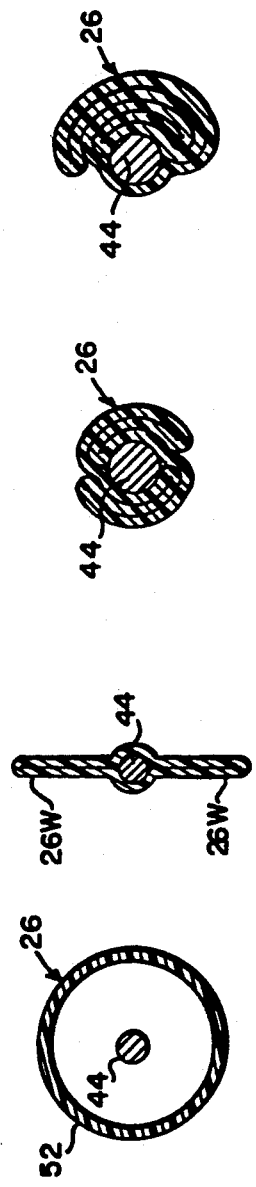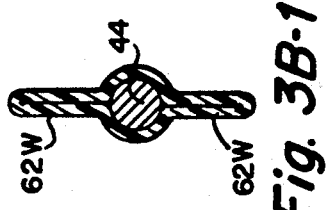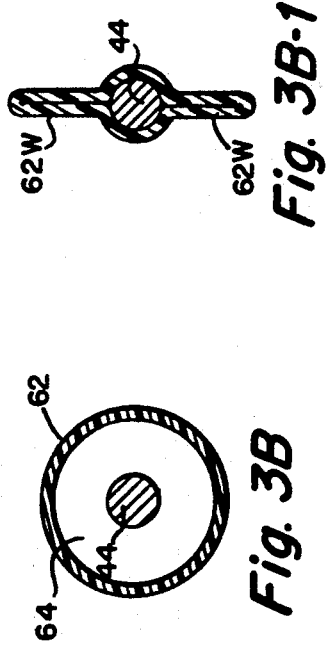

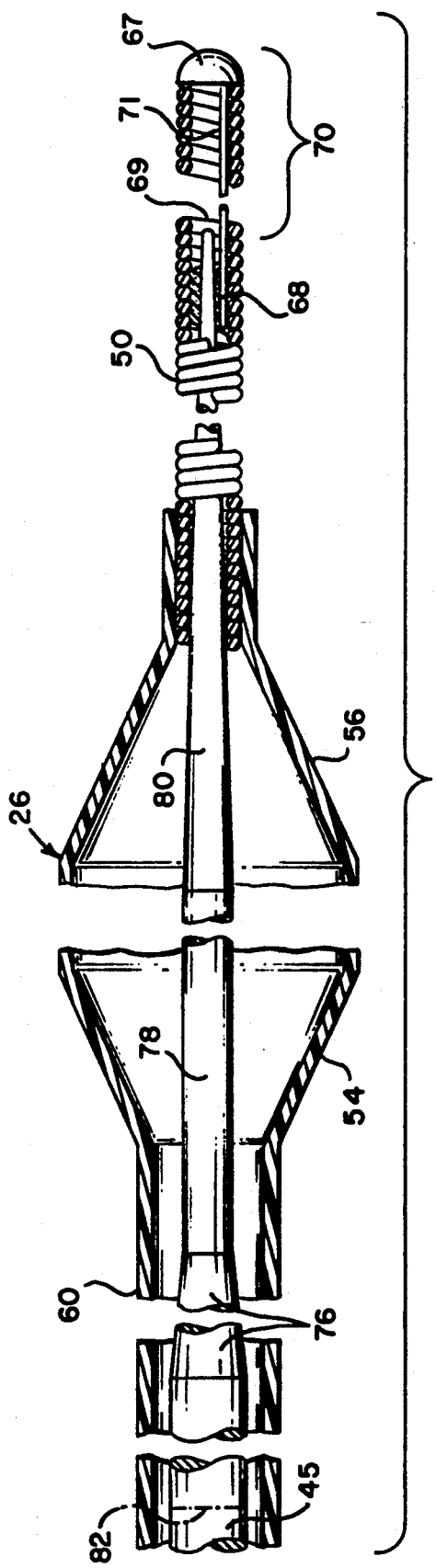
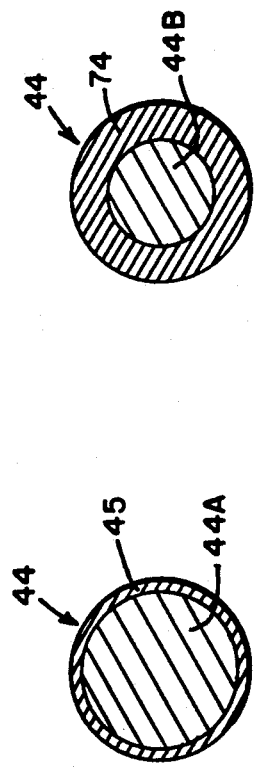

BALLOON DILATATION CATHETER WITH VARYING RADIOPACITY

RELATED APPLICATION

This application is a continuation in part of application Ser. No. 303,908 filed Jan. 30, 1989, now U.S. Pat. No. 4,917,088 which was a divisional of application Ser. No. 729,541 filed May 2, 1985 now U.S. Pat. No. 5,102,390.

FIELD OF THE INVENTION

This invention relates to improvements in catheters for performing balloon angioplasty procedures in stenosed blood vessels.

BACKGROUND OF THE INVENTION

Balloon angioplasty procedures have been used in recent years with increasing success in the treatment of obstructed arteries, such as the coronary arteries. The procedure involves advancing a catheter having a special balloon at its distal end to the location of the stenosis. The balloon portion of the catheter is placed, in its deflated condition, in the stenosis and then is inflated under high pressure to compress radially and outwardly the biological material such as plaque which forms the stenosis. Balloon dilatation systems of this type are illustrated in U.S. Pat. Nos. 4,195,637 and 4,323,071. In those situations in which balloon angioplasty can be used, its successful use avoids the greater risk of complex and expensive bypass surgery.

Not all arterial stenoses are treatable by balloon angioplasty. Among the types of vascular obstructions which have not been treatable with the angioplasty technology are those in which the passage through the stenosis is so narrow that the balloon angioplasty catheter cannot be inserted into the stenosis, even when the balloon is in its collapsed, deflated condition. Thus, where the opening in a stenosis was only enough to permit passage of a guide wire, but not enough to permit passage of a deflated angioplasty balloon, the procedure could not be performed. In order to enable balloon angioplasty to be performed in such narrowly stenosed arteries, low profile dilatation catheters have been developed. The low profile dilatation catheters typically are capable of assuming relatively low cross sectional dimensions, particularly in the region of the balloon, so that when the balloon is deflated, it may be inserted, in that configuration, into a tight stenosis. Typically, such low profile dilatation catheters incorporate a fixed guidewire as an integral part of the catheter. The guidewire forms part of or extends through the catheter and facilitates manipulation of the catheter so that it can be steered through branches in the patient's vasculature. Among the significant advances in such low profile catheters is that disclosed in U.S. patent application Ser. No. 303,908 filed Jan. 30, 1989. The probe-like catheter described in application Ser. No. 303,908 is very small in diameter and has a small diameter thin walled balloon at its distal portion. The catheter is constructed and arranged to be advanceable through the patient's vascular system and can be controlled and manipulated from its proximal end so that it can be steered selectively at forks in the vascular system. The main body of the catheter includes a flexible elongate hollow main shaft adapted to transmit torque from a proximal to the distal end of the catheter. The smaller diameter balloon support wire is attached to and extends from the distal end of the flexible hollow shaft. A helical spring is mounted to the distal portion of the support wire. The dilatation balloon is attached at its proximal end to the distal portion of the main shaft and the distal end of the balloon is attached to the proximal end of the helical spring. An inflation/deflation port is formed in the hollow main shaft distally of the proximal balloon connection to communicate with the interior of the balloon for inflating and deflating the balloon. A distal segment of the catheter which projects beyond the balloon includes the helical spring and a portion of the support wire. The support wire is tapered within the helical spring to provide progressively increasing flexibility in a distal direction. The distal end of the distal segment is adapted to be bent to a curve and enables the catheter to be selectively directed and steered by rotating the catheter from its proximal end. The balloon is very thin. The diameter of the collapsed folded balloon portion of the catheter is very small and defines a very small profile.

In order to enable steering of the catheter, a distal portion of the catheter is formed from a highly radiopaque material so that it is readily observable under X-ray fluoroscopy. Typically, such catheters have included radiopaque elements in the distal segment of the catheter, distally beyond the balloon. Additionally, small radiopaque markers may be disposed at other locations along the catheter to enable fluoroscopic determination of the location of other portions of the catheter, such as the proximal end of the balloon. In the catheter described in aforementioned application Ser. No. 303,908, the helical spring in the distal segment of the catheter is formed from a highly radiopaque alloy so that it appears quite dark on the fluoroscopic screen. Although providing a highly radiopaque portion of the catheter distally of the balloon is important in positioning the catheter, it is relatively short and provides relatively little indication of the shape and configuration of the artery or arteries in which the catheter is disposed. The configuration of the patient's coronary anatomy is important to the physician. Typically, during an angioplasty procedure, the physician will cause a radiographic contrast liquid to be emitted into the arteries being treated that so for a brief interval, the contour and anatomy of the arteries may be observed. Often the physician also activates a camera to make a permanent, replayable recording of the coronary anatomy. The injection of radiopaque contrast liquid also enables the physician to examine and determine the location and nature of the stenosis or stenoses to be treated. Although it would be desirable for the physician to have a continuous fluoroscopic indication of the coronary anatomy, that cannot be done because it would require continuous infusion of radiopaque contrast liquid. The amount of radiopaque contrast liquid that can be infused into a patient is limited. Therefore, it is believed that there is a need for a means by which the coronary anatomy may be observed continuously but without requiring continuous use of radiopaque contrast liquid. It is among the objects of the invention to provide a balloon dilatation catheter which facilitates fluoroscopic observation of the coronary anatomy through which a substantial portion of the catheter is disposed.

SUMMARY OF THE INVENTION

In accordance with the invention, the catheter, proximally of the highly radiopaque distal segment, is modified to include a moderately radiopaque material extending along a substantial portion of the distal length of the catheter at and proximally of the balloon. The moderately radiopaque portion which trails the highly radiopaque portion thus is observable as a light but discernible shade of grey and enables the physician to observe the contours and paths of the coronary anatomy through which the balloon has been placed. Additionally, by providing only a moderate radiopacity, the physician also may infuse radiopaque contrast liquid to observe further details of the coronary anatomy. By providing only a moderately radiopaque segment, there is no interference with the physician's observation of such details.

More particularly, in the present invention, the balloon support wire is coated with a thin film of radiopaque material, such as gold, to a degree sufficient to form a light grey, but discernible image on the fluoroscope. In a modification of the invention, the portion of the balloon support wire that extends through the balloon is not rendered radiopaque so that when the physician infuses radiopaque liquid into the region of the stenosis, where the balloon is located, no radiopacity will be caused by the balloon support wire. In that configuration, all of the radiopacity will be the result of the radiopaque contrast liquid, thus providing the physician with the most detailed, unobstructed picture possible.

Thus, it is among the general objects of the invention to provide a balloon dilatation catheter that is adapted to provide a radiopaque image, in varyinq shades of intensity, of a substantial portion of the arterial anatomy both proximally of and distally of the dilatation balloon.

A further object of the invention is to provide a catheter of the type described in which different portions of the catheter display different intensities of radiopacity under fluoroscopic observation.

DESCRIPTION OF THE DRAWINGS

The foregoing and other objects and advantages of the invention will be appreciated more fully from the following further description thereof, with reference to the accompanying drawings wherein:

FIG. 1 is a longitudinal, fragmented illustration of the dilatation catheter;

FIG. 2 is an enlarged longitudinal section of the portion of the dilatation catheter which includes the transition region from the proximal segment to the distal segment;

FIG. 2A is a cross-sectional illustration of the transition tube as seen along the line 2A—2A of FIG. 2;

FIG. 3 is an enlarged longitudinal sectional illustration of the balloon portion and distal segment of the dilatation catheter;

FIG. 3A is a sectional illustration of the catheter balloon as seen along the lines 3A—3A of FIG. 3;

FIG. 3A-1 is an illustration of the catheter balloon of FIG. 3A in an evacuated, collapsed configuration;

FIGS. 3A-2 and 3A-3 are illustrations of the collapsed dilatation catheter balloon with its wings wrapped about the support wire in an S-shaped configuration and a C-shaped configuration, respectively;

FIG. 3B is a sectional illustration of the sleeve extension of the catheter when the catheter is in an inflated condition;

FIG. 3B-1 is an illustration of the sleeve of FIG. 3B when in an evacuated, collapsed configuration;

FIG. 4 is an enlarged sectional illustration of the juncture of the balloon and the balloon extension sleeve;

FIG. 5 is a greatly enlarged cross sectional illustration of the core wire of the catheter illustrating, in exaggerated thickness, its radiopaque coating;

FIG. 6 is a cross-sectional illustration, in exaggerated detail, of a support wire clad with a radiopaque material; and FIG. 7 is a cross sectional illustration, in exaggerated detail, of the distal end of a balloon catheter having a support wire with a tapered distal portion and including a segment clad in radiopaque material.

DESCRIPTION OF THE PREFERRED EMBODIMENT

FIG. 1 illustrates a low profile balloon dilatation catheter adapted for use in the coronary arteries. The dilatation catheter 12 is of very slender construction having a cross-section approximately equal to that of a small diameter guide wire. The dilatation catheter 12 has a balloon 26 which, when collapsed, defines a small cross-sectional configuration so that it can pass through tight stenoses. In its collapsed configuration the balloon 26 as well as the remaining portions of the catheter 12 define an outer diameter corresponding to that of a small diameter guide wire. It should be understood, however, that the invention may be incorporated in catheters of other sizes as well.

The catheter 12, illustrated in FIG. 1, is of the order of about 150 centimeters when used in coronary arteries with a percutaneous femoral artery approach.

The catheter 12 has a relatively long proximal segment 28 which is formed from narrow, solid wall tubing, such as hypodermic tubing. In the illustrative embodiment, the proximal segment 28 may be of the order of 120 centimeters long. The proximal segment 28 is rigid torsionally so that it can transmit substantially fully to its distal end rotational motion imparted to the proximal end. As will be described, the distal tip of the catheter can be bent to a preset curve. Rotation applied to the catheter can be controlled to selectively direct and steer the curved distal end of the catheter as it is advanced. The proximal segment 28 also is flexible and can bend longitudinally to follow the curvature of the patient's arterial system. The proximal segment 28 of the catheter 12 may be sufficiently flexible that it can bend to follow the curve of a patient's aortic arch which has a radius of the order of between 2.5 to 3.5 inches in an adult. Alternately, it may be preferred to select a length for the proximal segment 28 so that it need not pass through the aortic arch.

As shown more clearly in enlarged FIG. 2, in the preferred embodiment of the invention the hollow tubular segment 28 has an outer diameter of 0.022 inches, a wall thickness of about 0.003 inches and an internal diameter passage 30 of 0.016 inches. A conventional fitting 32 is secured to the proximal end of segment 28 to facilitate connection with an inflation/deflation device, such as a syringe (not shown).

The catheter 12 includes a distal segment 34 which extends from the distal end of the proximal segment 28 to the distal end of the catheter 12. The distal segment 34 includes a narrow diameter elongate support wire 44 which is connected to and extends distally of the proximal segment 28. The support wire 44 is connected to the proximal tubing 28 by a short transition tube 36. The transition tube 36 is about three inches long and also is formed from slender, flexible hypodermic tubing with a smaller diameter than the proximal tube 28. In the illustrative embodiment, the transition tube 36 is formed from hypodermic tubing having an outer diameter of 0.015 inches, a wall thickness of 0.0035 inches and an inner diameter of 0.008 inches. The proximal end of the tubing 36 is received within the distal end of the internal passage 30 of the proximal segment 28 and is secured thereto as by soldering or brazing. The solid support wire 44 is attached to the distal end of the transition tube 36. The support wire 44, which in the illustrative embodiment is very slender, preferably 0.008 inches diameter, is received in the distal end of the passage 38 of the tubing 36 and is secured by soldering or brazing. The support wire 44 plugs the distal end of the tubing 36. In order to permit the balloon 26 to be inflated and deflated, the transition tube 36 is provided with apertures 46 on opposite sides of the tube wall to provide communication with the internal passages 38, 30 of the catheter. The apertures 46 may be defined by forming a pair of oval ports about 0.005×0.020 inches in the wall of the tubing 36. The support wire 44 provides support for the balloon 26 and also extends distally beyond the balloon 26, to form the core of a leader segment 48. The leader segment includes a helically wound radiopaque coil spring 50 which is attached to the distal end of the core wire 44 in a manner described below. The coil 50 may be formed from a platinum alloy, having a high percentage of platinum.

The balloon 26 is formed by molding high strength polymeric material in a manner which provides a thin balloon wall not greater than about 0.001 inches thickness and, preferably, having a thickness of the order of 0.0005 inches. The balloon may be manufactured as described in U.S. Pat. No. 4,490,421 issued Dec. 25, 1984 and reference is made thereto for further details concerning the manufacture of the balloon.

As shown in enlarged detail in FIG. 3, the balloon includes a main cylindrical portion 52. In the illustrative embodiment, the balloon 26 preferably has an outer diameter of 2.0 to 4.0 millimeters. As mentioned above, the balloon is formed from a high strength material which will not tend to stretch when inflated. The length of the balloon 26 may be of the order of 15 millimeters. The balloon is formed to include tapering portions 54, 56 at the proximal and distal ends respectively. The distal tapering portion 56 merges into a narrowed neck 58 which fits snugly about and against the proximal end of the coil spring 50. The distal neck 58 of the balloon 26 is adhesively attached to the coil spring 50. As will be described in further detail, the proximal end of the coil spring is soldered securely to the core wire at the region where the distal neck 58 of the balloon 26 is joined. The proximal tapering portion 54 merges into a narrowed proximal neck 60.

In order to communicate the interior of the balloon 26 with the inflation/deflation passages 30, 38 of the tubing, an extension sleeve 62 is adhesively attached to the proximal neck 60. The extension sleeve 62 extends proximally over the support wire 44. The proximal end of the extension sleeve 62 preferably is formed from the same material as the balloon 26 and is securely and adhesively attached to the outer surface of the transition tube 36, where it joins the main tube 28. The extension sleeve 62 defines an annular passage 64 about the support wire 44. The annular passage 64 provides communication between the apertures 46 and the interior of the balloon 26 for inflation and deflation of the balloon.

As shown in FIG. 3 the leader segment 48 which extends distally of the balloon 26 is of increasing flexibility in a distal direction to provide a relatively soft, flexible leading tip which reduces the chance of trauma or injury to the blood vessel. In the illustrative embodiment the leader segment is about 3 centimeters long. The coil spring 50 is soldered, at its proximal end to the support wire 44, as indicated at 66. The distal end of the support wire 44 also is soldered to the coil spring 50 as indicated at 68. Soldered joint 68 and the distal tip 69 of the support wire 44 terminate short of the distal tip of the coil spring 50. The distal tip 70 of the coil spring 50 may extend about five millimeters beyond the soldered joint 68 and defines a highly flexible bumper tip. A rounded weld bead 67 is formed at the distal tip of the spring 50. The leader segment 48 is of increasing flexibility in a distal direction. The support wire 44 is taper ground and, for example, may be ground smoothly to a 0.002 inch diameter at its distal tip 69.

The distal tip 70 of the coil spring 50 includes a flexible and bendable stainless steel shaping ribbon 71 which is secured to the distal tip 69 of the support wire at one end, and to the distal weld bead 67 at its other end. The shaping ribbon is of slender, rectangular cross section, of the order of 0.001 inches by 0.002 inches. The shaping ribbon is adapted to be bent to a desired curve and to retain that curve when relaxed. The preset curve enables the catheter 12 to be steered by rotation of the catheter from its proximal end. The catheter can be rotated to direct the prebent distal tip 70 in selective directions as desired within the patient's blood vessels.

The catheter also is provided with a radiopaque marker band 72 which preferably is formed from platinum. The marker band 72 is located proximally of the main portion of the balloon 26. In the illustrative embodiment it is securely attached to the support wire 44. The marker band 72 provides a means by which the physician can verify, fluoroscopically, the position of the balloon 26.

In order that the catheter may be passed through the lumen of a catheter which may guide the balloon catheter to the coronary arteries, the balloon 26 also must be collapsible to a shape and size which can be passed through the lumen of that guiding catheter. The invention accomplishes these objectives by using the slender, small diameter support wire 44 extending through the balloon and by using a balloon with a very thin but high strength wall. When the catheter 12 is to be inserted through the guiding catheter, the balloon 26 first is collapsed by applying suction, such as by a syringe, to the fitting 32. The balloon 26 and the extension sleeve 62 collapse, tending to form radially projecting wings as illustrated in FIGS. 3A-1 and 3B 1, respectively. The wings 62W and 26W wrap about the support wire 44 when the catheter is advanced through the main lumen of the guiding catheter. The wings 26W may wrap about the core wire 44 either in an S shaped configuration suggested in FIG. 3A-2 or in a C-shaped configuration shown in FIG. 3A-3. In either configuration the overall diameter through the collapsed and folded balloon portion of the catheter 12 includes six layers of the balloon material in addition to the diameter of the support wire 44. The balloon is formed from a high strength thin material having a wall thickness preferably not more than about 0.001". Thus, the aggregate diameter of six balloon layers plus the support wire is about 0.014 inches. The balloon thus is collapsible to a diameter which is about one fourth of its inflated diameter and which can pass easily through the main lumen of the guiding catheter.

In use a larger diameter guiding catheter through which the dilatation catheter 12 can be passed is inserted initially in the patient's arterial system, usually through the femoral artery, and is advanced through the aortic arch to locate the distal tip of the guiding catheter at the coronary ostium leading to the coronary artery or into the coronary artery to be treated. After the larger guiding catheter has been positioned the catheter 12 is advanced through the larger catheter with its balloon 26 in a collapsed configuration. The diameter of the catheter 12, in the illustrative embodiment, is about the same as a conventional guide wire. The dilatation catheter 12 thus can be advanced out of the distal opening of the guiding catheter with the balloon 26, in its collapsed configuration, and by advancing and rotationally manipulating the catheter through the patient's artery, can be inserted into and through the stenosis. The dilatation balloon 26 then may be inflated under pressure to expand forcefully the balloon 26 to its maximum diameter thereby enlarging the passageway through the stenosis.

When the balloon 26 has been inflated to enlarge the opening through the stenosis the balloon 26 is collapsed by aspirating the balloon. The catheter then may be withdrawn from the patient.

As described above, the catheter 12 is very flexible through its distal segment 34. The proximal segment 28 may be sufficiently flexible so that it can bend relatively easily through the aortic arch. It may be preferred, however, to dimension the catheter so that the juncture of the proximal segment 28 and distal segment 34 will be disposed proximally of the aortic arch. The bend from the aorta, into the coronary ostium and thereafter through the coronary arteries are sharper and shorter radiused. The length of the more flexible distal segment 34 is sufficient so that the balloon can reach deeply into the coronary arterial tree without requiring the stiffer proximal tubing 28 to pass through relatively sharp bends, such as the bend from a guide catheter to the coronary ostium. The distal segment 34, which consists substantially of the thin, flexible support wire 44 is able to make the relatively sharp bends with ease. Thus, the only portion of the catheter 12 which actually enters the coronary artery is that which includes the slender support wire 44. This support wire is very flexible and is more easily bent to be able to negotiate shorter radius bends encountered in the coronary arterial tree.

The catheter is highly steerable due in large measure to the solid wall of the tubing in the elongate proximal segment 28. The tubing is substantially torsionally rigid and tends to transmit substantially all of its rotation applied at the proximal end to the distal end. Although the intermediate segment of the catheter, which includes the slender 0.008 inch diameter wire is too small a diameter to effectively transmit torque over relatively long distances, the distal segment 34 is relatively short, preferably about 25 cm to 32 cm and, therefore, does not have too great of an adverse effect on the torque transmission from the proximal end of the catheter to the distal end. The distal segment preferably is no longer than about 25 cm to 32 cm, as compared to the solid wall tubular proximal segment which is approximately 143 cm to 150 cm long. Thus, by forming a bend in the distal tip 70 of the leading segment, the direction of the catheter 12 can be controlled by rotating the catheter from the proximal end.

The helical coil 50 and the marker band 72 are formed from highly radiopaque material, such as platinum or an alloy containing a high percentage of platinum. The coil 50 and marker band 72 thus are useful to indicate the location of the leader segment 48 and the proximal end of the balloon under fluoroscopy. It is important when performing an angioplasty that the physician be aware of the configuration and shape of the patient's coronary arteries. Typically, that is achieved by infusing radiopaque contrast liquid into the patient's artery and observing the patient's arteries under fluoroscopy for the brief interval that the radiopaque contrast liquid is in the artery, usually a few seconds. The physician thus is not provided with continuous information as to the configuration of the artery through which the catheter is passed. It would be desirable for the physician to have such information. Thus, in order to provide a means by which the physician may continually observe the orientation of the catheter and the configuration of the coronary artery through which the catheter is passed, the present invention provides an elongate radiopaque element extending along most or all of the distal segment 34 of the catheter. In the illustrative embodiment, the means for rendering the distal segment 34 radiopaque under fluoroscopy preferably is achieved by plating the support wire 44 with a radiopaque material, such as gold indicated schematically at 45 in FIG. 5. The support wire 44 may be coated fully along its length, from its junction with the tubing 36 distally through the balloon. Alternately, the region of the support wire 44 that extends through the balloon 26 may remain unplated so as not to be observable under fluoroscopy. Thus, when the catheter is disposed in the patient's arteries, a substantial length of the catheter, proximally of the balloon will be fluoroscopically observable, thus providing the physician with an indication of the contour and path of the coronary artery without requiring the infusion of radiopaque contrast liquid.

It is preferred that the radiopaque image provided along the length of the distal segment of the catheter is sufficiently dark so that it is observable under fluoroscopy but not so dark that it might interfere with the physician's more detailed observation of specific portions of the coronary anatomy by infusing radiopaque contrast liquid. Therefore, it is preferred that the means by which the distal segment 34 is rendered radiopaque is configured so that the fluoroscopic image that it creates is lighter than the darkest image achievable. Preferably, the degree of radiopacity is such as to present a "gray" image, as compared with the very dark image provided by the radiopaque coil 50 in the leader segment and the marker band 72. By providing a "gray" image, the physician is able to observe the path and orientation of the distal segment of the catheter 34 but without adversely obstructing the fluoroscopic image presented when radiopaque contrast liquid is infused into the artery. By way of example, the support wire 44 may be in the form of an inner core 44A plated with a layer 45 of gold of the order of 0.0002" to 0.0007" thick. The helical coil 50 is wound from a platinum alloy wire of the order of 0.003" in diameter. The marker band 72 may be formed from a platinum alloy ring. Thus, in the illustrative embodiment, the catheter would provide a fluoroscopic image in which the relatively short leader segment 48 and marker band 72 at the proximal end of the balloon 26 appear quite dark while the support wire 44 would appear as a lighter, gray image. It may be desirable to avoid any radiopaque means along the length of the balloon itself so that the region of the artery in which the balloon is located, namely, the critical region of the stenosis, can be observed completely and only with radiopaque contrast liquid without even minor fluoroscopic obstruction. That may be achieved simply by omitting the gold plating from that portion of the support wire 44 that extends through the balloon.

As an alternative to plating the support wire 44 with a highly radiopaque material such as gold, the moderately radiopaque, "gray" distal segment 34 may be achieved by forming the wire 44 itself from a moderately radiopaque alloy. For example, alloys of platinum, gold and ruthenium may be employed, selected as to maintain adequate torsional rigidity for the distal segment 34 of the catheter.

Yet another alternative for providing the moderately radiopaque segment is to make a support wire 44 from clad wire, as illustrated in enlarged and exaggerated cross sectional detail in FIG. 6. As shown in FIG. 6 a clad support wire 44 includes an inner core 44B about which is mechanically constricted a tubular cladding or jacket 74 of radiopaque material. The clad wire arrangement is preferable where it is desired to provide a thicker layer of radiopaque material about the inner core 44B. In contrast, conventional electroplating is a relatively time consuming procedure and the approximate maximum thickness to which gold plating may be made is of the order of 0.0005 inches. Considerably thicker layers may be achieved when using the clad wire. The clad wire is made by providing a core wire 44B and a thin wall tube of the metal from which the jacket 74 is to be made. By way of example, in order to make a support wire 0.008 inches in diameter the core wire 44B may be formed from stainless steel 0.003 inches in diameter. A length of gold hypodermic tubing, having a wall thickness in the order of 0.003 inches and an internal diameter just slightly greater than that of the inner core 44B, such as 0.0035 inches, is provided. The gold hypodermic tubing is slipped over the inner core 44B and together, they are drawn through a die having an outer diameter of 0.008 inches. The die constricts and draws the gold hypodermic tubing to a smaller diameter, tightly about the core wire 44B to secure them together mechanically into the composite wire. Similarly clad wire is available commercially from a number of commercial sources, such as the Sigmund Cohn Company in Mt. Vernon, N.Y. Of course, other materials and dimensions for the inner core 44B and jacket 74 may be selected, depending on the desired characteristics of the wire. By way of further example, the core wire 44B could be 0.006 inches in diameter with the cladding 74 having a final thickness in the order of 0.001 inches.

Among the advantages of using clad wire for the support wire 44 is that by grinding away segments of the radiopaque cladding, as desired, the radiopacity along the length of the support wire 44 may be varied as desired. For example, if it is desired to make a catheter in which the portion of the distal segment proximally of the balloon has a moderate "gray" radiopacity while the portion under the balloon has no radiopacity, of the cladding 74 can be ground away in the region of the support wire that will be disposed of within the balloon. In such an embodiment, it also may be desirable to provide a highly radiopaque marker band on the support wire 44 or in the region of the proximal and distal end of the balloon so as to highlight the ends of the balloon fluoroscopically.

FIG. 7 illustrates a further embodiment having a support wire with a step tapered configuration at its distal region as well as a clad configuration for the support wire. As shown in FIG. 7, the support wire 44 has a proximal portion 45 that is of a continuous diameter such as 0.008 inches for most of its length. The distal, approximately 8.5 centimeters of the support wire may be progressively tapered in a step tapered arrangement to provide for increasing flexibility in a distal direction. For example, the 0.008 inch diameter cylindrical support wire may include a tapering, conical segment 76, about 3 centimeters in length and tapering down to about 0.006 inches. The segment 76 then merges into a cylindrical barrel segment 78 of constant diameter (0.006 inches). The barrel segment 78 may be of the order of 2.5 centimeters in length. The distal most segment 80 may form a second conically tapered portion, tapering down to a distal tip approximately 0.002 inches in diameter. In this embodiment the proximal end of the coil spring may be attached to the segment 80 so that the proximal edge of the spring is approximately 1.8 centimeters from the distal tip of the segment 80. The balloon, which may be of the order of 2.5 centimeters long is attached adhesively at its distal end to the proximal end of the spring. The proximal end of the balloon is attached to the extension 60 in the region of the barrel segment 78. Such a core wire may be formed from nonradiopaque wire or from wire plated with a radiopaque metal or made from clad wire. In the plated configuration, the wire may be made with plated and unplated segments using conventional selected plating techniques relating to those in the plating art. Should it be preferred to use clad wire, a length of such clad wire may be provided and then its distal end may be centerless ground to provide the desired tapered configuration for the catheter. Depending on the final dimension, some or all of the cladding may be ground away at the distal region of the wire. For example, in the embodiment illustrated in FIG. 7, if the cladding were approximately 0.001 inches thick, the barrel segments 78, 80 would be free of cladding, the cladding having been ground away during the centerless grinding operation. The moderately radiopaque segment may have a proximal extremity about 35 cm from the distal tip of the wire 44, as suggested in phantom at 82 in FIG. 7. The support wire 44 is shown in exaggerated diameter, out of scale, for purpose of illustration.

From the foregoing, it will be appreciated that the invention provides improvements to balloon dilatation catheters, particularly those used in coronary angioplasty, by providing a means by which the physician may be provided with a continuous fluoroscopic indication of the configuration of the coronary artery through which the catheter passes along a substantial distance along a proximal segment of the catheter. Moreover, that object is achieved without unduly obstructing the fluoroscopic image of the coronary anatomy when it is desired to infuse radiopaque contrast liquid.

It should be understood, however, that the foregoing description of the invention is intended merely to be illustrative thereof and that other modifications, embodiments and equivalents of the invention will be apparent to those skilled in the art without departing from its spirit.

Having thus described the invention what I desire to claim and secure by letters patents is:

1. A balloon angioplasty catheter comprising:
  an elongate longitudinally flexible tubular proximal segment having a proximal end and a distal end;

an elongate distal segment extending distally beyond the distal end of the proximal segment, the distal segment being shorter and more flexible than the proximal segment and having nonuniform radiopacity;

a balloon carried by the distal segment;

the tubular proximal segment defining a lumen for communicating the proximal end of the catheter with the interior of the balloon to enable inflation and deflation of the balloon;

the distal segment comprising a support wire having a smaller diameter than the outer diameter of the distal end of the proximal segment and a highly radiopaque means carried by the support wire distally of the balloon;

moderately radiopaque means carried by the support wire proximally of the highly radiopaque means and extending along a substantial length of the support wire;

the balloon being supported on the support wire with the support wire extending through the balloon;

means for communicating the lumen of the proximal tubular segment with the interior of the balloon;

the proximal segment and support wire being sufficiently torsionally rigid so that when the catheter is in a configuration corresponding to that of a human aortic arch and with the distal segment in a coronary artery, the catheter is capable of transmitting controllably from its proximal to its distal end rotation applied at the proximal end.

2. A balloon angioplasty catheter as defined in claim 1 wherein the moderately radiopaque means extends through the balloon.

3. A catheter as defined in claim 1 wherein the moderately radiopaque means extends from the proximal end of the balloon toward the proximal end of the shaft and along a substantial portion of the catheter;

the region of the balloon being substantially free of radiopaque means.

4. A catheter as defined in claim 1 wherein the catheter is dimensioned and adapted to be inserted into the coronary arteries.

5. A catheter as defined in any one of claim 1-3 wherein the moderately radiopaque means comprises a plating of radiopaque material on the elongate flexible support wire.

6. A balloon angioplasty catheter as defined in any one of claim 1-3 wherein the moderately radiopaque means comprises a cladding of radiopaque material on the support wire.

7. A catheter as defined in any one of claims 1-3 wherein the support wire is formed from a moderately radiopaque material.

8. A catheter as defined in claim 5 further comprising a short highly radiopaque element carried by the catheter adjacent the proximal end of the balloon.

9. A catheter as defined in claim 5 wherein the distal segment is between about 25 cm to 35 cm in length.

10. A balloon catheter as defined in claim 6 further comprising a short highly radiopaque element carried by the catheter adjacent the proximal end of the balloon.

11. A catheter as defined in claim 6 wherein the distal segment is between about 25 cm to 35 cm in length.

* * * * *